United States Patent [19]

Loev et al.

[11] 4,435,395

[45] Mar. 6, 1984

[54] N-SUBSTITUTED 1,4-DIHYDROPYRIDAZINES AND PHARMACEUTICAL COMPOSITIONS

[75] Inventors: Bernard Loev, Scarsdale; Howard Jones, Ossining, both of N.Y.; James R. Shroff, Riverside, Conn.

[73] Assignee: USV Pharmaceutical Corporation, Tarrytown, N.Y.

[21] Appl. No.: 471,958

[22] Filed: Mar. 3, 1983

[51] Int. Cl.³ .................. A61K 31/535; C07D 413/06
[52] U.S. Cl. ............................ 424/248.5; 424/248.51; 424/248.52; 424/248.54; 424/248.55; 544/114
[58] Field of Search ............................... 544/114, 122; 424/248.5, 248.51, 248.52, 248.54, 248.55

[56] References Cited

U.S. PATENT DOCUMENTS 4,258,042  3/1981  Loev et al. ......................... 544/122

*Primary Examiner*—Robert W. Ramsuer

[57] ABSTRACT

Compounds of the formula:

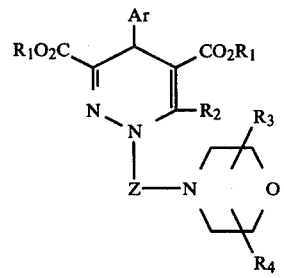

which are useful as antihypertensive agents are disclosed.

23 Claims, No Drawings

N-SUBSTITUTED 1,4-DIHYDROPYRIDAZINES AND PHARMACEUTICAL COMPOSITIONS

This invention relates to new anti-hypertensive agents and more particularly to certain new substituted 1,4-dihydropyridazines possessing useful anti-hypertensive activity.

Substituted 1,4-dihydropyridines are known and have been described in the literature as vasodilating agents. 1,4-Dihydropyridines having vasodilating activity are characterized by the presence of alkyl substituents in the 2 and 6 positions of the pyridine ring and carbalkoxy groups in the 3,5-positions usually with a substituent, most commonly phenyl or substituted phenyl, in the 4-position. To increase the water-solubility of these compounds, M. Iwanami, et al. [Chem. Pharm. Bull. 27 (6), 1426–1440 (1979)] described the effect of N-substitution of the pyridine ring nitrogen with, inter alia, aminoalkylene groups such as pyrrolidinoethyl and dimethylaminoethyl. Thus, water-solubility determinations with compounds such as diethyl 1,4-dihydro-4-(3-nitrophenyl)-2,6-dimethyl-1-(2-pyrrolidinoethyl)-3,5-pyridinedicarboxylate and the corresponding 1-(2-dimethylaminoethyl) compound were determined as was the potency thereof as vasodilators but these compounds were determined to be of lower potency than known compounds such as the corresponding 1-ethoxymethyl compound.

Japanese specification No. 70767/76 describes as anti-hypertensive and vasodilating agents 1,4-dihydropyridines of the formula

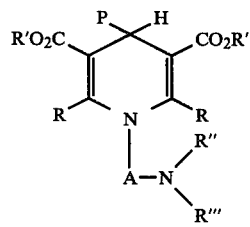

in which R is alkyl; P is substituted (mono or di-) phenyl, pyridyl, furyl, or thienyl in which the substituents are H, halogen, —CN, —NO$_2$, —NH$_2$, —N(CH$_3$)$_2$, carboxyl, methoxy, ethoxy, butoxy, sulfonyl, methylsulfonyl or acetyl; R' is alkyl, aralkyl, methyl, ethyl, isopropyl, t-butyl, ethoxyethyl, benzyl, phenethyl, or 4-methoxybenzyl; A is alkylene; and R" and R''' are each alkyl and, when taken together, form a pyrrolidine ring with the N to which they are attached.

U.S. Pat. No. 4,258,042 describes N-morpholinodihydropyridines of the formula:

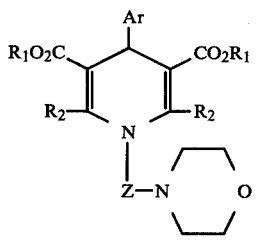

wherein Ar is heteroaryl, cycloalkyl or

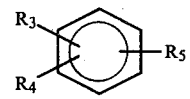

wherein each of R$_3$, R$_4$ and R$_5$ is H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and R$_3$ and R$_4$, when taken together, form a methylenedioxy; Z is alkylene containing 1 to about 5 carbon atoms in the principal chain; and each R$_1$ and R$_2$ is alkyl; and acid addition salts thereof.

The new compounds of the present invention are N-substituted dihydropyridazines of the formula:

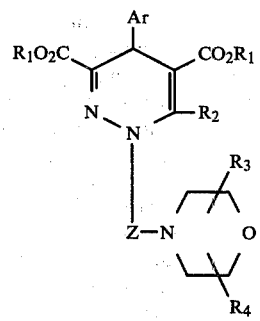

wherein Ar is heteroaryl, cycloalkyl or

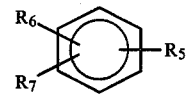

wherein each of R$_5$, R$_6$ and R$_7$ is H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and R$_5$ and R$_6$, when taken together, form a methylenedioxy; Z is alkylene containing 1 to about 5 carbon atoms in the principal chain; R$_3$ and R$_4$ are each H or alkyl; and each R$_1$ and R$_2$ is alkyl; and acid addition salts thereof.

The total number of carbon atoms in each such hydrocarbyl substituent can range up to about 10. The substituent "Z" contains up to about 5 carbons in the principal chain, i.e. the straight chain of carbons between the terminal valences, but can be branched in that methyl and ethyl substituents can be present on the principal chain. Thus, the alkylene chain Z can contain a total number of carbon atoms greater than 5, preferably no more than about 8.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene and substituted heterocycles.

The preferred compounds are those in which the hydrocarbyl radicals contain up to about 7 carbon atoms when aliphatic and up to about 10 carbon atoms when aromatic, e.g., phenyl, tolyl and naphthyl.

The particularly preferred compounds of the invention are those in which Z is —CH$_2$CH$_2$— and Ar is a nitrophenyl or a trifluoromethylphenyl group, especially 2-trifluoromethylphenyl or 2-nitrophenyl.

The new compounds of the invention can be prepared by art-recognized procedures from known starting compounds as described, for example, in the literature hereinbefore described. The following procedure constitutes a particularly convenient preparative method:

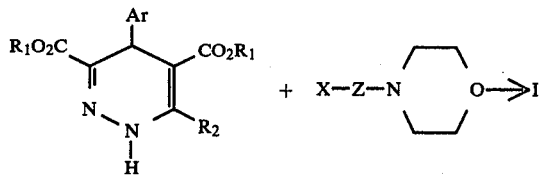

The reaction can be carried out in a solvent in the presence of sodium hydride, or any alkali metal hydride or alkoxide as is commonly employed in condensation reactions. The reaction is effected in two steps, the first metallation with the alkali metal compound, and the second, condensation with the halide, "X", containing compound, while is usually chloride. The hydrides are convenient since the progress of the metallation reaction can be followed by observing the evolution of hydrogen gas. The metallation step is normally carried out at room temperature. The reaction mixture thereafter is heated at elevated temperature, e.g. at steam bath temperature at or about 100° C., or above up to about 150° C. depending on the boiling point of the selected solvent, and the halide compound is then added, usually in controlled amounts in dropwise fashion and, after addition is completed, the reaction mixture is digested by heating at the elevated temperature.

The product is then obtained in the usual fashion, as by cooling to cause precipitation or evaporation of the solvent to obtain the product as a residue.

The starting compounds of formula II are prepared by reacting a compound of the formula

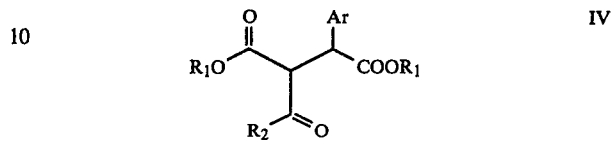

with hydrazine. Alternatively, compounds of formula I can be prepared by reaction of compounds of formula IV with a compound of the formula

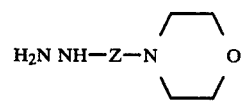

The present new compounds have a chiral center at the carbon to which the Ar group is attached and therefore exist in stereoisomeric forms, i.e., in the "S" and "R" forms. The "S" or "R" form can be separated from one another by known methods of resolution. Of course, mixtures of the isomers can be used for therapeutic purposes without resolution.

Employing these procedures, a variety of new N-morpholinoalkyl 1,4-dihydropyridazines of the following formula can be prepared:

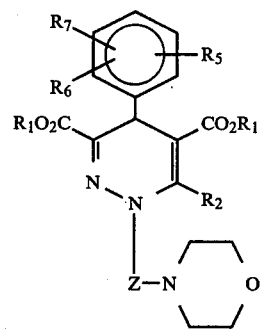

| Z | R$_2$ | R$_1$ | R$_7$ at 4 position | R$_6$ at 3 position | R$_5$ at 2 position |
|---|---|---|---|---|---|
| CHCH$_3$ | CH$_3$ | C$_2$H$_5$ | H | H | H |
| CHCH$_3$ | CH$_3$ | C$_2$H$_5$ | H | CH$_3$ | H |
| CH$_2$CH$_2$ | CH$_3$ | C$_2$H$_5$ | H | H | H |
| CH(CH$_3$)CH$_2$ | C$_2$H$_5$ | C$_2$H$_5$ | H | H | Cl |
| CH$_2$CH$_2$ | CH$_3$ | i-C$_3$H$_7$ | H | CN | H |
| CH$_2$CH$_2$ | CH$_3$ | C$_2$H$_5$ | H | H | NO$_2$ |
| CH$_2$CH$_2$ | CH$_3$ | C$_2$H$_5$ | H | OH | H |
| CH$_2$CH$_2$ | C$_3$H$_7$ | CH$_3$ | H | H | CF$_3$ |
| CH(CH$_3$) | C$_4$H$_9$ | C$_2$H$_5$ | H | OCH$_3$ | H |
| (CH$_2$)$_3$ | C$_6$H$_{13}$ | C$_2$H$_5$ | H | COOH | H |
| CH$_2$CH$_2$ | i-C$_4$H$_9$ | CH$_3$ | OCH$_3$ | H | H |
| CH$_2$CH$_2$ | CH$_3$ | C$_2$H$_5$ | H | OCH$_3$ | OCH$_3$ |
| (CH$_2$)$_5$ | CH$_3$ | C$_2$H$_5$ | H | CH$_3$ | CH$_3$ |
| CH$_2$CH$_2$ | CH$_3$ | C$_4$H$_9$ | H | H | CH$_2$C$_6$H$_5$ |
| CH$_2$CH$_2$ | CH$_3$ | C$_6$H$_{13}$ | H | H | C(CH$_3$)$_3$ |
| CH(CH$_3$)CH$_2$ | CH$_3$ | i-C$_4$H$_9$ | H | H | C$_6$H$_5$ |
| CH$_2$CH$_2$ | CH$_3$ | C$_2$H$_5$ | H | H | H |
| CH$_2$CH$_2$ | CH$_3$ | C$_2$H$_5$ | Cl | Cl | Cl |
| CH$_2$CH$_2$ | CH$_3$ | C$_2$H$_5$ | Cl | H | Cl |

-continued

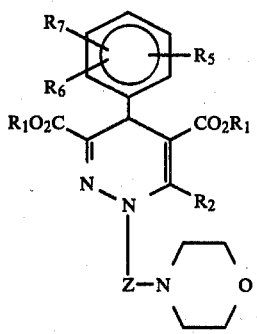

| Z | $R_2$ | $R_1$ | $R_7$ at 4 position | $R_6$ at 3 position | $R_5$ at 2 position |
|---|---|---|---|---|---|
| $CH_2CH_2$ | $CH_3$ | $C_2H_5$ | Cl | H | Cl |
| $CH_2CH_2$ | $CH_3$ | $C_2H_5$ | $OCH_3$ | H | $CH_2=CH-CH_2$ |
| $CH_2CH_2$ | $CH_3$ | $C_2H_5$ | H | H | H |
| $CH_2CH_2$ | $CH_3$ | $C_2H_5$ | H | $CH_3$ | H |
| $CH_2CH_2$ | $CH_3$ | $C_2H_5$ | H | H | H |
| $CH_2CH_2$ | $CH_3$ | $C_2H_5$ | H | H | H |
| $CH_2CH_2$ | $CH_3$ | $C_2H_5$ | H | $CH_3$ | H |
| $CH_2CH_2$ | $CH_3$ | $C_2H_5$ | H | $CH_3$ | $CH_3$ |
| $CH_2CH_2$ | $CH_3$ | $C_2H_5$ | H | H | H |
| $CH_2CH_2$ | $CH_3$ | $C_2H_5$ | H | H | H |
| $CH_2CH_2$ | $CH_3$ | $C_2H_5$ | H | $CH_3$ | H |
| $CH_2CH_2$ | $CH_3$ | $C_2H_5$ | H | H | Cl |
| $CH_2CH_2$ | $CH_3$ | $C_2H_5$ | H | CN | H |
| $CH_2CH_2$ | $CH_3$ | $C_2H_5$ | $NO_2$ | H | H |
| $CH_2CH_2$ | $CH_3$ | $C_2H_5$ | H | OH | H |
| $CH_2CH_2$ | $CH_3$ | $C_2H_5$ | H | $CF_3$ | H |
| $CH_2CH_2$ | $CH_3$ | $C_2H_5$ | H | $OCH_3$ | H |
| $CH_2CH_2$ | $CH_3$ | $C_2H_5$ | H | COOH | H |
| $CH_2CH_2$ | $CH_3$ | $C_2H_5$ | $OCH_3$ | H | H |
| $CH_2CH_2$ | $CH_3$ | $C_2H_5$ | H | $OCH_3$ | $OCH_3$ |
| $CH_2CH_2$ | $CH_3$ | $C_2H_5$ | H | H | $OCH_3$ |
| $CH_2CH_2$ | $CH_3$ | $C_2H_5$ | $OCH_3$ | H | $CH_2=CH-CH_2-$ |
| $CH_2CH_2$ | $CH_3$ | $C_2H_5$ | H | H | $COOCH_3$ |
| $CH_2CH_2$ | $CH_3$ | $C_2H_5$ | $OCH_3$ | H | $COOCH_3$ |
| $CH_2CH_2$ | $CH_3$ | $C_2H_5$ | H | H | $-(CH_2)_4-$ |
| $CH_2CH_2$ | $CH_3$ | $C_2H_5$ | H | H | $NH_2$ |

Corresponding compounds wherein the morpholine moiety is substituted by lower alkyl groups can also be prepared by substitution of the corresponding alkyl morpholine starting compound.

The compounds of this invention are characterized by high anti-hypertensive activity with little, if any, adverse side effects.

The present new heterocyclic compounds are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycolic, gluconic, succinic, arylsulfonic, e.g. p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds are particularly useful as anti-hypertensive agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-hypertensive agents and the dosage level is of the same order of magnitude as is generally employed with these other therapeutic agents. The therapeutic dosage will generally be from 10 to 750 milligrams per day and higher, although it may be administered in several different dosage units. Tablets containing from 10 to 250 mg. of active agent are particularly useful.

The following examples further illustrate the invention.

EXAMPLE 1

Diethyl 1,4-dihydro-4-(2-trifluoromethylphenyl)-6-methyl-1-(2-morpholinoethyl)-3,5-pyridazine dicarboxylate To a slurry of sodium hydride (2.6 g.; 55 mmole; 50:50 oil dispersion) in dry, distilled DMF (50 ml) under nitrogen atmosphere is added a solution of diethyl 1,4-dihydro-4-(2-trifluoromethylphenyl)-6-methyl-3,5-pyridazine dicarboxylate (19.9 g.; 50 mmole) in DMF (125 ml). After hydrogen bubbling ceases, the reaction mixture is warmed in a water bath for ½ hour, and a toluene (200 ml) solution of N-(2-chloroethyl)morpholine (60 mmole) is added dropwise. The reaction mixture is stirred at 110°–115° for 4 hours.

The reaction mixture is then cooled, vacuum filtered, and the filtrate concentrated in vacuo. The resulting paste is taken up in refluxing hexane and allowed to crystallize. Recrystallization from hexane affords solid product.

Diethyl 1,4-dihydro-4-(2-nitrophenyl)-6-methyl-1-(2-morpholinoethyl)-3,5-pyridazine dicarboxylate This compound is prepared using the procedure of Example 1 from diethyl 1,4-dihydro-4-(2-nitrophenyl)-6-methyl-3,5-pyridazine dicarboxylate and N-(2-chloroethyl)morpholine.

EXAMPLE 3

The hydrochloride salts of the products of Examples 1 and 2 are obtained by dissolving in alcohol saturated with hydrogen chloride gas. Evaporation to dryness, followed by exhaustive extraction of the residue with ether gave the hydrochloride salts as residue.

EXAMPLE 4

A. Ethyl 2-(o-trifluoromethylbenzylidene)acetoacetic ester

A mixture of o-trifluoromethyl benzaldehyde (8.7 g.), ethylacetoacetate (6.5 g.), piperidine (0.2 ml), and acetic acid (0.6 ml) in 100 ml of toluene is heated to reflux while the water formed is removed by Dean-Stark apparatus. Reaction is continued overnight. Evaporation of solvent gives 12 g. of oil by product.

B. 2-Acetyl-3-(2-trifluoromethylphenyl)-4-nitropentanedioic acid diethyl ester

Ethyl-2-(2-trifluoromethylbenzylidene) acetoacetic ester (12.0 gms.; 0.042 mole) and ethyl nitroacetate (5.5 gms.; 0.042 mole) are dissolved in 150 ml of ethanol and the reaction mixture refluxed at 80° C. for a period of 10 hours. The solvent is removed in vacuo and the residue crystallized from 2-propanol to afford the desired product.

C. 2-Acetyl-3-(2-trifluoromethylphenyl)-4-oxo-pentanedioic acid diethyl ester

The nitro compound (8.38 gms.; 0.02 mole) in 50 ml of anhydrous methanol is treated with one equivalent of NaOMe (1.08 gms.; 0.02 mole) and stirred for 10 minutes to form the nitronate salt. The methanolic solution is then cooled to $-78°$ C. and a stream of ozone/oxygen (ozone generated with a Welsbach ozonator) passed through until the solution was slightly blue. After 30 minutes, the reaction mixture is purged with a $N_2$ stream to remove excess $O_3$, and then treated with 5 ml of $(CH_3)_2S$ at $-78°$ C. and slowly allowed to come to room temperature. After standing for 16 hours, the volatile material is removed by rotatory evaporation, the residue taken up in ether, washed with brine and then dried (anh. $MgSO_4$) and concentrated to afford an oil.

D. Diethyl 1,4-dihydro-4-(2-trifluoromethylphenyl)-6-methyl-3,5-pyridazine dicarboxylate The diketone (5.4 gms.; 0.013 mole) and hydrazine hydrate (5 ml) in ethanol are stirred at room temperature for 10 minutes and then heated under reflux for a further ½ hour. The reaction mixture is poured into water, the oily yellow product extracted with $CH_2Cl_2$, the $CH_2Cl_2$ extract dried over anh. $MgSO_4$, and the solvent evaporated to obtain a crude product as a yellow oil. Crystallization from ethanol (decolorizing carbon) affords the cyclized pyridazine.

E. Diethyl 1,4-dihydro-4-(2-trifluoromethylphenyl)-6-methyl-1-(2-morpholinoethyl)-3,5-pyridazine dicarboxylate To a slurry of 2.3 gms. NaH (50%, 0.05 mole) in 50 ml of dry DMF in a 1-liter 3-necked flask equipped with a stirrer, dropping funnel, condenser and bubbler at the end of the condenser is added 9.5 gms. (0.05 mole) of the dihydropyridazine dissolved in 100 ml DMF. After the evolution of $H_2$ gas ceases, the reaction mixture is warmed on a water bath for period of 1 hour. From the dropping funnel, a toluene solution of morpholinoethyl chloride (obtained by the neutralization of 18.6 gms. (0.1 mole) of N-(2-chloroethyl)morpholine hydrochloride with 25% NaOH) is introduced into the dihydropyridazine solution. The reaction mixture is heated for a period of 4–5 hours at 80°–100° C., then allowed to cool, the NaCl and unreacted NaH is filtered off and the solvents removed from the filtrate.

The residue is refluxed with 100–200 ml hexane for a period of 2–4 hours and the hexane solution filtered. The solid that separates when the hexane solution is allowed to cool is collected. Two recrystallizations from 2-propanol affords the final product.

What is claimed is:

1. A compound of the formula

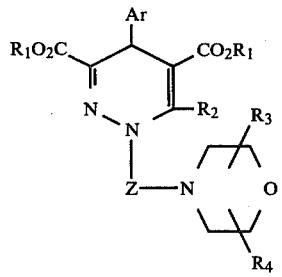

wherein Ar is heteroaryl, cycloalkyl or

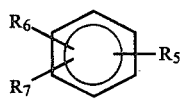

wherein each of $R_5$, $R_6$ and $R_7$ is H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and $R_5$ and $R_6$, when taken together, form a methylenedioxy; Z is alkylene containing 1 to about 5 carbon atoms in the principal chain; $R_3$ and $R_4$ are each H or alkyl; and each $R_1$ and $R_2$ is alkyl; and acid addition salts thereof.

2. The compound according to claim 1 wherein Ar is a monosubstituted phenyl group and Z is —CH$_2$—CH$_2$—.

3. The compound according to claim 1 wherein heteroaryl is thienyl, furyl, thiazolyl, pyridyl or quinolinyl.

4. The compound according to claim 1 wherein Ar is a trifluoromethylphenyl.

5. The compound according to claim 1 wherein Ar is a trifluoromethylphenyl and Z is —CH$_2$—CH$_2$—.

6. Diethyl 1,4-dihydro-4-(2-trifluoromethylphenyl)-6-methyl-1-(2-morpholinoethyl)-3,5-pyridazinedicarboxylate.

7. A pharmaceutically-acceptable acid addition salt of the compound of claim 6.

8. An anti-hypertensive composition comprising a compound according to claim 1 and a carrier.

9. An antihypertensive compound of the formula

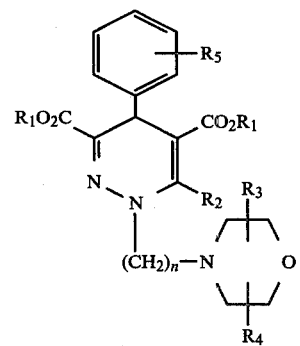

wherein $R_1$ and $R_2$ are each lower alkyl, n is the integer 2, 3 or 4, $R_3$ and $R_4$ are each hydrogen or alkyl and $R_5$ is H, trifluoromethyl, methoxy, or nitro and pharmaceutically-acceptable salts thereof.

10. The compound according to claim 9 wherein $R_5$ is trifluoromethyl.

11. The compound according to claim 9 wherein $R_5$ is nitro.

12. The compound according to claim 9 wherein n is 2.

13. An antihypertensive compound of the formula

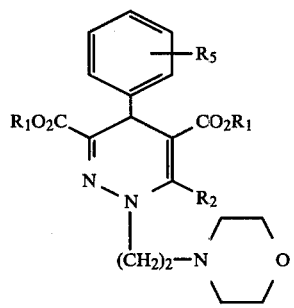

wherein $R_1$ and $R_2$ are each lower alkyl and $R_5$ is H, trifluoromethyl, nitro, or methoxy and pharmaceutically-acceptable salts thereof.

14. The compound according to claim 13 wherein $R_5$ is trifluoromethyl.

15. The compound according to claim 13 wherein $R_5$ is nitro.

16. The compound according to claim 13 wherein $R_5$ is methoxy.

17. The compound according to claim 14 wherein each $R_1$ is ethyl or methyl and $R_2$ is methyl.

18. The compound according to claim 15 wherein each $R_1$ is ethyl or methyl and $R_2$ is methyl.

19. The compound according to claim 16 wherein each $R_1$ is ethyl or methyl and $R_2$ is methyl.

20. The compound according to claim 13 wherein the $R_5$ substitution is at the 2 position.

21. A pharmaceutically-acceptable salt of the compound according to claim 17.

22. A pharmaceutically-acceptable salt of the compound according to claim 18.

23. A pharmaceutically-acceptable salt of the compound according to claim 19.

* * * * *